| United States Patent [19] | [11] | 4,281,134 |
|---|---|---|
| Ten Haken et al. | [45] | Jul. 28, 1981 |

[54] DERIVATIVES OF CERTAIN PHENYLIMINOMETHYLPYRIDINES

[75] Inventors: Pieter Ten Haken, Eastling, Near Faversham; Shirley B. Webb, Sheldwich, Near Faversham; Graham C. Smith, Sittingbourne, all of England

[73] Assignee: Shell Oil Company, Houston, Tex.

[21] Appl. No.: 111,734

[22] Filed: Jan. 14, 1980

Related U.S. Application Data

[63] Continuation-in-part of Ser. No. 60,716, Jul. 26, 1979, abandoned.

[30] Foreign Application Priority Data

Aug. 8, 1978 [GB] United Kingdom ............... 32523/78

[51] Int. Cl.$^3$ .......................................... C07D 213/36
[52] U.S. Cl. .................................... 546/334; 424/263; 424/267; 546/194; 546/276; 546/330
[58] Field of Search ............... 546/330, 334, 194, 276

[56] References Cited

U.S. PATENT DOCUMENTS

| 3,196,158 | 7/1965 | Bencze | 546/330 X |
| 3,531,476 | 9/1970 | Miyano et al. | 542/424 OR |
| 4,046,916 | 9/1977 | Negrevergne | 424/263 X |

OTHER PUBLICATIONS

Hamana et al., Chem. Abstracts vol. 55, col. 18723 (1961).
Schulze, Chem. Abstracts vol. 58, col. 12509 (1963).
Marey, Chem. Abstracts, vol. 70 abst. 68072(a) (1969).
Person et al., Chem. Abstracts, vol. 73, abst. 126456 (1970).
Barnes et al., Chem. Abstracts, vol. 79, abst. 78550e (1973).
Krohnke et al., Chem. Ber. vol. 92. pp. 22–36 (1959).
Rich, Chemical Abstracts, vol. 71, abst. 80463g (1969).
Hay et al., Chemical Abstracts, vol. 84, abst. 156,212 (1976).

*Primary Examiner*—John D. Randolph

[57] ABSTRACT

Derivatives of certain phenyliminomethylpyridines, useful as fungicides and/or plant growth regulators.

3 Claims, No Drawings

DERIVATIVES OF CERTAIN PHENYLIMINOMETHYLPYRIDINES

This application is a continuation-in-part of application Ser. No. 60,716, filed on July 26, 1979, now abandoned.

DESCRIPTION OF THE INVENTION

This invention relates to certain derivatives of phenyliminomethylpyridines, described by the class formulae:

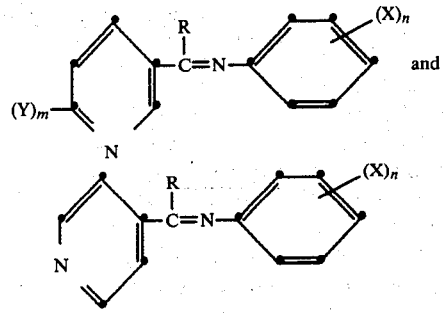

the derivatives consisting of four subclasses:

(1) derivatives of formula I wherein m is zero, n is zero and R is alkylthio;

(2) derivatives of formula I wherein m is zero, n is one or two, and R is alkyl, alkoxy, alkoxyalkoxy, alkylthio, cycloalkyloxy, cyano, optionally substituted phenylthio, triazolyl, (n-butyl)-amino, di(n-butyl)amino, 1-piperidinyl, di(n-propyl)amino, (n-nonyl)amino, di(3-methylpropyl)amino; 3,5-dimethyl-piperidin-1-yl, and X is alkyl or halogen, with the provisos that (a) when R is alkoxy and X is alkyl, n is one;
(b) when R is isopropoxy, X is halogen, and n is two, 3-chloro, 4-fluoro is excluded;
(c) when R is alkoxy, n is two, one of X is halogen and the other is alkyl, 3-methyl, 4-bromo is excluded;
(d) when R is alkylthio; X is alkyl and n is one, 4-alkyl is excluded.

(3) derivatives of formula I wherein R is isopropoxy, isopropylthio, m is one, Y is chlorine, and $(X)_n$ is 4-chloro;

(4) derivatives of formula II wherein
(a) R is isopropoxy and $(X)_n$ is
  (i) 4-chloro;
  (ii) 2,4-dichloro;
  (iii) 3,4-dichloro;
  (iv) 2,3-dichloro;
  (v) 3,5-chloro;
(b) R is cyano and $(X)_n$ is 4-chloro.

The alkyl alkoxy and alkoxyalkoxy moieties represented by R suitably contain from one to twenty carbon atoms and are either straight-chain or branched-chain in configuration. In the alkoxyalkoxy moieties represented by R, the oxygen atom linking the alkyl moiety to the alkyleneoxy moiety can be located in any position on the chain. Alkyl moieties represented by X suitably contain from one to four carbon atoms and are either straight-chain or branched-chain in configuration. The alkylthio moieties represented by R suitably contain from one to five carbon atoms and are of straight-chain or branched-chain configuration. The cycloalkoxy moieties represented by R suitably contain from three to six carbon atoms. Suitable substituents on the phenylthio moieties represented by R are halogen; nitro; cyano; amino; straight-chain or branched-chain alkyl, alkyloxy and alkylthio of from one to six carbon atoms. Suitable halogens are chlorine, bromine and fluorine.

Particularly useful as fungicides are:
4'-chlorophenylimino-C-(cyano)methyl-3-pyridine;
4'-chlorophenylimino-C-(n-propoxy)methyl-3-pyridine;
4'-chlorophenylimino-C-(n-butoxy)methyl-3-pyridine;
4'-chlorophenylimino-C-(cyclohexyloxy)methyl-3-pyridine;
4'-chlorophenylimino-C-(methylthio)methyl-3-pyridine;
4'-chlorophenylimino-C-(tert-butylthio)methyl-3-pyridine;
4'-chlorophenylimino-C-(di-n-butylamino)methyl-3-pyridine;
4'-chlorophenylimino-C-(n-piperidinyl)methyl-3-pyridine;
4'-chlorophenylamino-C-(isopropoxy)methyl-3-pyridine;
2',4'-dichlorophenylimino-C-(isopropoxy)methyl-3-pyridine;
3',4'-dichlorophenylimino-C-(isopropoxy)methyl-3-pyridine.

These compounds have been found to be fungicides, and/or regulators of plant growth.

The compounds according to the invention may be prepared by any suitable adaptation of known methods. A preferred method for the preparation of the 3-pyridyl species consists in reacting a nicotinic anilide with a thionyl halide, preferably thionyl chloride, and converting the resulting phenylimino-C-(halo)-methyl-3-pyridine to the desired product by treating it with a compound R-Q, wherein R has the defined meaning and Q is hydrogen or an alkali metal.

The invention is further illustrated by the following Examples. In each case, the identity of the product was confirmed by appropriate chemical and spectral analyses.

EXAMPLE 1

4'-chlorophenylimino-C-(cyano)methyl-3-pyridine (1)

A stirred mixture of 4.65 g of nicotinic-4'-chloroanilide and 20 ml of thionyl chloride was heated under reflux for 2 hours. Excess thionyl chloride was removed under reduced pressure and the residue was treated with 50 ml of dry pyridine. To the stirred solution was added 3.58 g of dry cuprous cyanide. After 15 minutes, pyridine was removed under reduced pressure, and the residue was extracted with warm acetone. Evaporation of the solvent from the extract gave 1, as a yellow crystalline solid, melting point 73°–75° C.

EXAMPLE 2

4'-chlorophenylimino-C-(isopropoxy)methyl-3-pyridine (2)

A stirred mixture of 7 g of nicotinic-4'-chloroanilide and 22.5 ml of thionyl chloride was heated under reflux for 2 hours. Excess thionyl chloride was removed under reduced pressure, and the residue was suspended in 75 ml of dry dimethoxyethane. A solution of 2.43 g of sodium in 100 ml of dry isopropyl alcohol was added all at once, and the mixture was stirred for one hour at room temperature and then heated under reflux for 16 hours. Solvents were removed under reduced pressure, and the residue treated with ether; the ethereal solution was washed with water and dried over MgSO$_4$. After removal of the solvent, the residue was subjected to column chromatography on silica gel, eluting with ether/hexane (1/1 v/v). Recrystallization from 60/80 petroleum spirit gave 2, as a colorless crystalline solid, melting point 71°–72.5° C.

EXAMPLE 3

4'-chlorophenylimino-C-(n-propoxy)methyl-3-pyridine (3)

A stirred mixture of 7 g of nicotinic-4'-chloroanilide and 22.5 ml of thionyl chloride was heated under reflux for 2 hours. Excess thionyl chloride was removed under reduced pressure, and the residue was suspended in 75 ml dry dimethoxyethane. A solution of 2.42 g of sodium in 100 ml of dry n-propanol was added all at once, and the mixture was stirred for one hour at room temperature, and then heated under reflux for 16 hours. Solvents were removed under reduced pressure, the residue was treated with chloroform, the chloroform solution was washed with water and dried over $MgSO_4$. After removal of the solvent, the residue was subjected to column chromatography on silica gel, eluting with chloroform/ethyl acetate (4/1 v/v) to give 3, as an oil.

EXAMPLE 4

4'-chlorophenylimino-C-(n-butoxy)methyl-3-pyridine (4)

A stirred mixture of 7 g of nicotinic-4'-chloroanilide and 22.5 ml of thionyl chloride was heated under reflux for 2 hours. Excess thionyl chloride was removed under reduced pressure, and the residue suspended in 75 ml of dry dimethoxyethane. A solution of 2.42 g of sodium in 100 ml of dry n-butanol was added all at once, and the mixture was stirred at room temperature for one hour, and then heated under reflux for 16 hours. Solvents were removed under reduced pressure, and the residue was treated with chloroform. The chloroform solution was washed with water and dried over $MgSO_4$. After removal of the solvent, the residue was subjected to column chromatography on silica gel, eluting with ether/hexane (1/1 v/v). Recrystallization from 40/60 petroleum spirit gave 4, as colorless crystals, melting point 53°–54° C.

EXAMPLE 5

4'-chlorophenylimino-C-(cyclohexyloxy)methyl-3-pyridine (5)

A mixture of 7 g of nicotinic-4'-chloroanilide and 22.5 ml of thionyl chloride was stirred and heated under reflux for 2 hours. Excess thionyl chloride was removed under reduced pressure, and the residue was treated with 100 ml of dry pyridine. To the stirred solution was added 3.15 g of distilled cyclohexanol, and the mixture was heated in an oil bath at 100° C. for 6½ hours. After removal of the solvent under reduced pressure, the residue was treated with ether. The ethereal solution was washed with water and dried over $MgSO_4$. After removal of the solvent, the residue was subjected to column chromatography on silica gel, eluting with ether/hexane (1/1 v/v) to give 5, as a viscous oil.

EXAMPLE 6

4'-chlorophenylimino-C-(methylthio)methyl-3-pyridine (6)

2.485 g of nicotinic-4'-chlorothioanilide was suspended in 40 ml of dry dimethoxyethane. 0.48 g of sodium hydride (50% dispersion in oil) was added, and the mixture was stirred until a clear solution was obtained. 1.42 g of methyl iodide was then added and the mixture was stirred at ambient temperature for 19 hours. Solvent was removed under reduced pressure, and the residue was treated with ether. The ethereal solution was washed with water and dried over $MgSO_4$. After removal of the solvent, the residue was subjected to column chromatography on silica gel, eluting with chloroform, to give 6, as a solid, melting point 59°–60.5° C.

EXAMPLE 7

4'-chlorophenylimino-C-(tert-butylthio)methyl-3-pyridine (7)

A stirred mixture of 7 g of nicotinic-4'-chloroanilide and 22.5 ml of thionyl chloride was heated under reflux for 2 hours. Excess thionyl chloride was removed under reduced pressure, and the residue treated with 100 ml of dry pyridine. 5.4 g of tert-butyl mercaptan was added, and the mixture was stirred and heated in an oil bath at 100°–110° C. for 16 hours. Solvent and volatiles were removed under reduced pressure, and the residue was treated with ether. The ethereal solution was washed with water and dried over $MgSO_4$. After removal of solvent, the residue was subjected to column chromatography on silica gel, eluting with ether/hexane (1:1 v/v) to give 7, as a bright yellow crystalline solid, melting point 85°–87° C.

EXAMPLE 8

4'-chlorophenylimino-C-(n-butylamino)methyl-3-pyridine (8)

A stirred mixture of 7 g of nicotinic-4'-chloroanilide and 22.5 ml of thionyl chloride was heated under reflux for 2 hours. Excess thionyl chloride was removed under reduced pressure, and the residue was suspended in 75 ml of dry dimethoxyethane. 10.8 g of n-butylamine was added, and the mixture was stirred at ambient temperature for 24 hours. Solvent was removed under reduced pressure, and the residue was treated with ether. The ethereal solution was washed with water and dried over $MgSO_4$. After removal of solvent, the residue was subjected to column chromatography on silica gel, eluting with ether/hexane (2:1 v/v). Recrystallization from 60/80 petroleum spirit gave 8, melting point 65°–67° C.

EXAMPLE 9

4'-chlorophenylimino-C-(di-n-butylamino)methyl-3-pyridine (9)

A mixture of 7 g of nicotinic-4'-chloroanilide and 22.5 ml of thionyl chloride was stirred and heated under reflux for 2 hours. Excess thionyl chloride was removed under reduced pressure, and the residue was suspended in 150 ml of dry dimethoxyethane. 19.5 g of di-n-butylamine was added, and the mixture was stirred for 2 hours at ambient temperature. The solvent was removed under reduced pressure, and the residue was treated with ether. The ethereal solution was washed with water and dried over $MgSO_4$. After removal of the solvent, the residue was subjected to column chromatography on silica gel, eluting with ether/hexane (1:1 v/v), to give 9 as a viscous oil.

EXAMPLE 10

4'-chlorophenylimino-C-(N-piperidinyl)methyl-3-pyridine (10)

A stirred mixture of 7 g of nicotinic-4'-chloroanilide and 22.5 ml of thionyl chloride was heated under reflux for 2 hours. Excess thionyl chloride was removed under reduced pressure, and the residue was suspended in 100 ml of dry dimethoxyethane. 9 g of piperidine was added, and the mixture was stirred at ambient temperature for 16 hours. Solvent was removed under reduced pressure, and the residue was treated with ether. The ethereal solution was washed with water and dried over MgSO$_4$. After removal of solvent, the residue was subjected to column chromatography on silica gel, eluting with ether/hexane (1:1 v/v), to give 10, as a viscous oil.

EXAMPLES 11–61

In an analogous manner as described in the previous examples, the following compounds were prepared:

TABLE I

| Example No. | Compound No. | Compound | Melting Point (°C.) |
|---|---|---|---|
| 11 | 11 | 4'-chlorophenylimino-C-(ethoxy)methyl-3-pyridine | oil |
| 12 | 12 | 4'-chlorophenylimino-C-(methoxy)methyl-3-pyridine | oil |
| 13 | 13 | 4'-chlorophenylimino-C-(triazolyl)methyl-3-pyridine | 100–103 |
| 14 | 14 | 4'-chlorophenylimino-C-(2-butoxy)methyl-3-pyridine | oil |
| 15 | 15 | 4'-chlorophenylimino-C-(iso-butoxy)methyl-3-pyridine | 34–35 |
| 16 | 16 | 4'-chlorophenylimino-C-(n-octyloxy)methyl-3-pyridine | 39–40 |
| 17 | 17 | 4'-chlorophenylimino-C-(n-dodecyloxy)methyl-3-pyridine | oil |
| 18 | 18 | 4'-chlorophenylimino-C-(isopropylthio)methyl-3-pyridine | 59–61 |
| 19 | 19 | 4'-chlorophenylimino-C-(p-chlorophenylthio)methyl-3-pyridine | 96–99 |
| 20 | 20 | 4'-chlorophenylimino-C-(di-n-propylamino)methyl-3-pyridine | oil |
| 21 | 21 | 4'-chlorophenylimino-C-(n-nonylamino)methyl-3-pyridine | 58–59 |
| 22 | 22 | 4'-chlorophenylimino-C-(methethoxy)methyl-3-pyridine | oil |
| 23 | 23 | 4'-fluorophenylimino-C-(isopropoxy)methyl-3-pyridine | 43–44.5 |
| 24 | 24 | 3',5'-dichlorophenylimino-C-(isopropoxy)methyl-3-pyridine | 55–56 |
| 25 | 25 | 3',5'-dichlorophenylimino-C-(isopropylthio)methyl-3-pyridine | 36–37.5 |
| 26 | 26 | 4'-fluorophenylimino-C-(isopropylthio)methyl-3-pyridine | 21–22 |
| 27 | 27 | 3',4'-dichlorophenylimino-C-(isopropoxy)-methyl-3-pyridine | 53–55 |
| 28 | 28 | 3',4'-dichlorophenylimino-C-(isopropylthio)methyl-3-pyridine | 42–44 |
| 29 | 29 | Phenylimino-C-(isopropylthio)methyl-3-pyridine | oil |
| 30 | 30 | 4'-bromophenylimino-C-(isopropoxy)methyl-3-pyridine | 54–56 |
| 31 | 31 | 4'-bromophenylimino-C-(isopropylthio)methyl-3-pyridine | 78–80 |
| 32 | 32 | 2',4'-dichlorophenylimino-C-(isopropoxy)methyl-3-pyridine | 47–49 |
| 33 | 33 | 3'-chloro-4'-fluorophenylimino-C-(isopropylthio)methyl-3-pyridine | oil |
| 34 | 34 | 2',4'-dichlorophenylimino-C-(isopropylthio)methyl-3-pyridine | oil |
| 35 | 35 | 3'-chlorophenylimino-C-(isopropoxy)methyl-3-pyridine | 54 |
| 36 | 36 | 4'-chlorophenylimino-C-(isopropoxy)methyl-4-pyridine | 72–74 |
| 37 | 37 | 2',4'-dichlorophenylimino-C-(isopropoxy)methyl-4-pyridine | |
| 38 | 38 | 3',4'-dichlorophenylimino-C-(isopropoxy)methyl-4-pyridine | |
| 39 | 39 | 2',3'-dichlorophenylimino-C-(isopropoxy)methyl-4-pyridine | 74–75 |
| 40 | 40 | 4'-chlorophenylimino-C-(cyano)-methyl-4-pyridine | 110–112 |
| 41 | 41 | 4'-chlorophenylimino-C-(di-2-methylpropylamino)methyl-3-pyridine | oil |
| 42 | 42 | 4'-chlorophenylimino-C-(3,5-dimethylpiperidin-1-yl)methyl-3-pyridine | 97–98 |
| 43 | 43 | 2',3'-dichlorophenylimino-C-(isopropoxy)methyl-3-pyridine | 35–36 |
| 44 | 44 | 2'-chlorophenylimino-C-(n-butoxy)methyl-3-pyridine | oil |
| 45 | 45 | 2'-chloro-4'-methylphenylimino-C-(n-butoxy)-3-pyridine | 58 |
| 46 | 46 | 2'-chloro-4'-methylphenylimino-C-(isopropylthio)-3-pyridine | oil |
| 47 | 47 | 3'-chloro-4'-methylphenylimino-C-(n-butoxy)-3-pyridine | 42 |
| 48 | 48 | 3'-chloro-4'-methylphenylimino-C-(isopropylthio)-3-pyridine | oil |
| 49 | 49 | 2'-methyl-4'-chlorophenylimino-C-(n-butoxy)-3-pyridine | 43.5 |
| 50 | 50 | 2'-methyl-4'-chlorophenylimino-C-(isopropylthio)-3-pyridine | oil |
| 51 | 51 | 2'-chloro-5'-methylphenylimino-C-(n-butoxy)-3-pyridine | 32.5 |
| 52 | 52 | 6-chloro-4'-chlorophenylimino-(C-isopropylthio)methyl-3-pyridine | 61–62 |
| 53 | 53 | 4'-methylphenylimino-C-(n-butoxy)methyl-3-pyridine | 54–55 |
| 54 | 54 | 3'-methylphenylimino-C-(n-butoxy)methyl-3-pyridine | 41 |
| 55 | 55 | 2'-methylphenylimino-C-(n-butoxy)methyl-3-pyridine | oil |
| 56 | 56 | 2',3'-dichlorophenylimino-C-(n-butoxy)methyl-3-pyridine | 45 |
| 57 | 57 | 2',5'-dichlorophenylimino-C-(isopropylthio)methyl-3-pyridine | 53 |
| 58 | 58 | 2',6'-dichlorophenylimino-C-(n-butoxy)methyl-3-pyridine | oil |
| 59 | 59 | 2',6'-dichlorophenylimino-C-isopropylthio)-3-pyridine | oil |
| 60 | 60 | 6'-chloro-4'-chlorophenylimino-C-(isopropoxy)methyl-3-pyridine | 57–59 |
| 61 | 61 | 3',5'-dichlorophenylimino-C-(isopropoxy)methyl-4- | 60–61 |

TABLE I-continued

| Example No. | Compound No. | Compound | Melting Point (°C.) |
|---|---|---|---|
| 62 | 62 | pyridine 4'-chlorophenylimino-(C-methyl) methyl-3-pyridine | 70-72 |

All structures, configurations and purities are supported by NMR spectroscopic data.

Fungicidal Activity

The fungicidal activity of the compounds according to the invention was investigated by the following foliar spray tests:

(1) Activity against vine downy mildew (Plasmopara viticola-Pv.a)

The test was a direct antisporulant one using a foliar spray. The lower surface of leaves of whole vine plants were inoculated by spraying with an aqueous suspension containing $10^5$ zoosporangia per milliliter four days prior to treatment with the test compound. The inoculated plants were kept for 24 hours in a high humidity compartment, 48 hours at glasshouse ambient temperature and humidity and then returned for a further 24 hours to high humidity. The plants then were dried and infected leaves detached and sprayed on the lower surfaces at a dosage of 1 kilogram of active material per hectare using a track sprayer. After drying, the petioles of the sprayed leaves were dipped in water and the leaves returned to high humidity for a further 72 hours incubation, followed by assessment. Assessment was based on the percentage of the leaf leaf area covered by sporulation compared with that on control leaves.

(2) Activity against vine downy mildew (Plasmopara viticola—Pv.t)

The test was a translaminar protectant one using a foliar spray. The upper surfaces of leaves of whole vine plants were sprayed at a dosage of 1 kilogram of active material per hectare using a track sprayer. The lower surfaces of the leaves were then inoculated, up to 6 hours after treatment with the test compound, by spraying with an aqueous suspension containing $10^5$ zoosporangia per milliliter. The inoculated plants were kept for 24 hours in a high humidity compartment, 4 days at glasshouse ambient temperature and humidity and then returned for a further 24 hours to high humidity. Assessment was based on the percentage of the leaf area covered by sporulation compared with that on control leaves.

(3) Activity against vine grey mould (Botrytis cinerea—B.c.)

The test was a direct eradicant one using a foliar spray. The under-surfaces of detached vine leaves were inoculated by pipetting ten large drops of an aqueous suspension containing $5 \times 10^5$ conidia per milliliter on to them. The inoculated leaves were kept uncovered overnight during which time the drops containing the conidia slowly dry. By this time the fungus had penetrated the leaf and a visible necrotic lesion sometimes was apparent where the drop was made. The infected regions were sprayed directly with a dosage of one kilogram of active material per hectare using a track sprayer. When the spray had dried the leaves were covered with petri dish lids and the disease allowed to develop under the moist conditions. The extent of the necrotic lesion beyond the original drop together with the degree of sporulation was compared with that on control leaves.

(4) Activity against potato late blight (Phytophthora infestans—P.i.e.)

The test was a direct eradicant one using a foliar spray. The upper surfaces of the leaves of potato plants (12—18 centimeters high, in monopots) were inoculated by spraying with an aqueous suspension containing $5 \times 10^3$ zoosporangia per milliliter 16-19 hours prior to treatment with the test compound. The inoculated plants were kept overnight at high humidity and then allowed to dry before spraying at a dosage of one kilogram of active material per hectare using a track sprayer. After spraying, the plants were returned to high humidity for a further period of 48 hours. Assessment was based on a comparison between the levels of disease on the treated and control plants.

(5) Activity against barley powdery mildew (Erysiphe graminis-E.g.)

The test measured the direct antisporulant activity of compounds applied as foliar spray. For each compound about 40 barley seedlings were grown to the one-leaf stage in a plastic pot of sterile potting compost. Inoculation was effected by dusting the leaves with conidia of *Erysiphe graminis.* spp. hordei. 24 hours after inoculation the seedlings were sprayed with a solution of the compound in a mixture of acetone (50%), surfactant (0.049%) and water using a track sprayer. The rate of application was equivalent to 1 kilogram of active material per hectare. First assessment of disease was made 5 days after treatment, when the overall level of sporulation on the treated pots was compared with that on control pots.

(6) Activity against wheat brown rust (Puccinia recondita—P.r.)

The test was a direct antisporulant one using a foliar spray. Pots containing about 25 wheat seedlings per pot, at first leaf stage, were inoculated by spraying the leaves with an aqueous suspension, containing $10^5$ spores per milliliter plus a little Triton X-155, 20-24 hours before treatment with the compound under test. The inoculated plants were kept overnight in a high humidity compartment, dried at glass-house ambient temperature and then sprayed at a dosage of one kilogram of active material per hectare using a track sprayer. After treatment, the plants were kept at glass-house ambient temperature and assessment made about 11 days after treatment. Assessment was based on the relative density of sporulating pustules per plant compared with that on control plants.

(7) Activity against broad bean rust (Uromyces fabae—U.f.)

The test was a translaminar antisporulant one using foliar spray. Pots containing one plant per pot were inoculated by spraying an aqueous suspension, containing $5 \times 10^4$ spores per milliliter plus a little Triton X-155, onto the undersurface of each leaf 20-24 hours before treatment with test compound. The inoculated plants were kept overnight in a high humidity compartment, dried at glass-house ambient temperature and then sprayed on the leaf upper surface, at a dosage of one kilogram per hectare of active material using a track sprayer. After treatment the plants were kept at glass-house temperature and assessment made 11-14 days after treatment. Symptoms were assessed on the relative density of sporulating pustules per plant compared with that on control plants.

(8) Activity against rice leaf blast (Pyricularia oryzae—P.o.)

The test was a direct eradicant one using a foliar spray. The leaves of rice seedlings (about 30 seedlings per pot) were sprayed with an aqueous suspension containing $10^5$ spores per milliliter 20-24 hours prior to treatment with the test compound. The inoculated plants were kept overnight in high humidity and then allowed to dry before spraying at a dosage of one kilogram of active material per hectare using a track sprayer. After treatment, the plants were kept in a rice compartment at 25°-30° C. and high humidity. Assessments were made 4-5 days after treatment and were based on the density of necrotic lesions and the degree of withering when compared with control plants.

(9) Activity against rice sheath blight (Pellicularia sasakii—P.s.)

The test was a direct eradicant one using foliar spray. 20-24 hours prior to treatment with the test compound, rice seedlings (about 30 seedlings per pot) were sprayed with five milliliters of an aqueous suspension containing 0.2 gram of crushed sclerotia/mycelium per milliliter. The inoculated plants were kept overnight in a humid cabinet maintained at 25°-30° C., followed by spraying at a dosage of one kilogram of active material per hectare. The treated plants then were returned to high humidity for a further period of 3-4 days. With this disease brown lesions are seen that start at the base of the sheath and extended upwards. Assessments were made on the number and extent of the lesions when compared with the controls.

(10) Activity against potato late blight (Phytophthora infestans—Pi.p.)

The test measured the direct protectant activity of compounds applied as a foliar spray. Tomato plants, cultivar Ailsa Craig, 1-15 cms high, in monopots were used. The whole plant was sprayed at a dosage of 1 kilogram of active material per hectare using a track sprayer. The plant then was inoculated up to 6 hours after treatment with the test compound, by spraying with an aqueous suspension containing $5 \times 10^3$ zoosporangia per milliliter. The inoculated plants were kept in high humidity for 3 days. Assessment was based on a comparison between the levels of disease on the treated and control plants.

The extent of disease control was expressed as a control rating according to the criteria:
0 = less than 50% disease control
1 = 50-80% disease control
2 = greater than 80% disease control The disease control ratings are given in Table II for the compounds described in the previous Examples.

TABLE II

| Organism | Compounds Having The Rating* | |
|---|---|---|
| | 2 | 1 |
| Pv.a | 1, 4, 6, 12 | 3, 17, 20, 47 |
| Pv.t | 3, 4, 10, 11, 13, 31 | 17, 22, 39, 41 |
| B.e. | 11, 21 | 32 |
| Pi.e. | 10, 19 | 12 |
| Pi.p. | | 2 (systemic), 17 (systemic), 22 (systemic) |
| E.g. | 1, 2 (systemic), 3, 4, 5, 6, 7, 8, 9, 10, 11, 12, 14, 15, 16, 17, 18, 20 (systemic), 22, 23, 24, 25, 26, 27, 28, 29, 30 (systemic), 31, 32, 33, 34, 35, 36, 37, 38, 41, 42, 43, 44, 45, 46, 47, 48, 49, 50, 51, 52, 53, 54, 55, 56, 57, 58, 59 | 13, 19, 62 |
| P.r. | 1, 40, 41 | 4, 6, 36 |
| U.f. | | 7, 33, 57 |
| P.o. | 39 | 7, 17, 23, 28, 29 |
| P.s. | 3, 5, 9 | 7, 15 |

*Otherwise, the test compounds had a "0" rating with respect to the organisms.

Plant Growth Regulating Activity

The plant growth regulating properties of compounds of the invention were investigated using the following test:

The plants used in the evaluation of the compounds were determinate soya bean cultivars (e.g. Fiskeby V).

Liquid formulations of the compounds were applied to plants at an early stage of flower development. The formulations used consisted of 60% water and 40% acetone which contained 0.4% TRITON X155, and amounts of the test compound to give a spray application equivalent to 0.5, 1.0 and 2.0 kilograms per hectare, respectively.

The soya bean seeds were inoculated with a commercial strain of Rhizobium ("Nitrogerm", Root Nodule Pty., Ltd., Australia) prior to sowing in a loam/grit (5/1 v/v) mixture in 5 inch diameter pots. Plants were maintained at 21°-25° C. under a 14 hour day length and watered by sub-irrigation. Treatments were as foliar applications to three plants for each dose of the test material, applied in a volume equivalent to 632 liters per hectare using a fixed "jaw" nozzle. After treatment the plants were set out in a randomized block design. Height (centimeters), phytotoxicity and other physiological effects were recorded one week after treatment. After a further three weeks the total number of pods per plant was recorded. Results were derandomized and mean vaues calculated and expressed as a percentage of the untreated controls. The pod numbers thus obtained are given in Table III.

TABLE III

| Compound | Dose (kg/ha) | | |
|---|---|---|---|
| | 0.5 | 1.0 | 2.0 |
| 11 | 89 | 115 | 121 |
| 12 | 138 | 161 | 138 |
| 3 | 100 | 131 | 138 |
| 4 | 123 | 146 | 154 |
| 14 | 146 | 115 | — |
| 15 | 115 | 131 | 146 |
| 16 | 123 | 146 | 138 |
| 18 | 138 | 146 | 169 |
| 25 | 113 | 117 | 117 |
| 27 | 121 | 121 | 132 |
| 31 | 129 | 138 | 125 |
| 22 | 103 | 127 | — |
| 60 | 103 | 112 | 118 |
| 61 | 97 | 106 | 136 |
| 38 | 106 | 112 | 133 |
| 62 | 118 | 136 | 105 |

The plant growth regulating properties of compounds of the invention also were investigated by means of a test designed to show their effect as abscission agents, as follows:

French bean (cv. Canadian Wonder) were used as the indicator species for abscission activity. French bean seeds were sown at the rate of 2 per 8 centimeter pot in sterilized loam. Plants were maintained at 20° C. under 14 hours daylength and watered by subirrigation. At the first trifoliate leaf stage of development, the laminae of the primary leaves were removed. 48 hours after removal of the laminae, liquid formulations of the test compounds were applied. The formulation used consisted of 90% water and 10% acetone which contained 0.4% TRITON X155 and amounts of the test compound to give spray application of 50, 250, 1000, and 2000 rpm of the compound, respectively.

Treatments were as foliar applications to "run off" using a fixed nozzle. After treatment the plants were set out in randomized block design.

The number of petioles which had absicissed from the main stem were recorded three, five and ten days after treatment. Phytotoxicity and any other physiological effects were also recorded 10 days after treatment. Results were derandomized and the mean value of the three replicates per treatment calculated.

The obtained results are given in Table IV as either no abscission activity (O), or greater than 75% activity (+) as compared with untreated controls.

TABLE IV

| Compound | (Dose ppm) | | | |
| --- | --- | --- | --- | --- |
| | 50 | 250 | 1000 | 2000 |
| 16 | 0 | 0 | — | + |
| 17 | 0 | 0 | — | + |
| 18 | + | | + | |
| 30 | 0 | 0 | + | + |
| 31 | 0 | 0 | + | + |
| 34 | 0 | 0 | 0 | + |
| 44 | 0 | 0 | + | + |
| 45 | 0 | + | + | + |
| 47 | 0 | 0 | 0 | + |
| 53 | 0 | + | + | + |
| 55 | 0 | 0 | 0 | + |

As has been shown, most of the compounds of the invention are fungicidal, with some exhibiting useful plant growth regulating properties, including inducing an increase in the number of pods in soya bean plants, and effecting abscission of foliage and/or fruits from plants.

The invention accordingly includes the compounds per se; a method for controlling unwanted fungi and a method for influencing the growth of plants, by applying to the locus in question an effective dosage of one or more of the compounds of the invention, and compositions containing one or more of the compounds of the invention, the composition being adapted for the intended purpose. Suitably, the composition is applied to provide from about 0.1 to about 10 kilograms of the compound(s) per hectare, and is most effective when applied to the foliage of the plants at an early stage of growth. Control of fungi ordinarily is effected at similar dosage rates, by application of the compound(s) of the invention to seeds of crops subject to attack by fungi, or the soil in which the plants are to be grown or are growing, and/or the foliage of such plants. In either case, it is normal agrochemical practice to mix with the active material a carrier and/or a surface-active agent, and accordingly, the compositions of the invention comprise the compound(s) of the invention together with either or both a carrier and a surface-active agent.

The term "carrier" as used herein means a solid or fluid material, which my be inorgaic or organic and of synthetic or natural origin, with which the active compound is mixed or formulated to facilitate its application to the plant, seed, soil or other object to be treated, so its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or fungicides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5∝5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may contain other ingredients, for example, protective colloids such as gelatin, glue, casin, gums, cellulose ethers, and polyvinyl alcohol; thixotropic agents, e.g., bentonites, sodium polyphosphates; stabilizers such as ethylene diamine tetra-acetic acid, urea, triphenyl phosphate; other fungicides or pesticides; and stickers, for example non-volatile oils.

The compositions of the invention may also contain other biologically active ingredients, for example, other compounds possessing pesticidal, especially insecticidal, acaricidal, herbicidal or fungicidal properties.

We claim:
1. A phenyliminomethylpyridine of the formula:

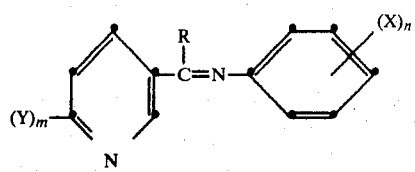

(1) m is zero, n is zero and R is alkylthio of from one to five carbon atoms;
(2) m is zero, n is one or two, and R is alkyl, alkoxy or alkoxyalkoxy of from one to twenty carbon atoms; alkylthio of from one yo five carbon atoms; cycloalkyloxy of from three to six carbon atoms; cyano, optionally substituted phenylthio, triazolyl, (n-butyl)amino, di(n-butyl)amino, 1-piperidinyl, di(n-propyl)amino, (n-nonyl)amino, di(3-methyl-propyl)amino; 3,5-dimethyl-piperidin-1-yl; and X is alkyl of from one to four carbon atoms or halogen, with the provisos that
   (a) when R is alkoxy and X is alkyl, n is one;
   (b) when R is isopropoxy, X is halogen, and n is two, 3-chloro, 4-fluor is excluded;
   (c) when R is alkoxy, n is two, one of X is halogen and the other is alkyl, 3-methyl, 4-bromo is excluded;
   (d) when R is alkylthio; X is alkyl and n is one, 4-alkyl is excluded;
(3) R is isopropoxy, is isopropylthio, m is one, Y is chlorine, and (X)$_n$ is 4-chloro.

2. A phenyliminomethylpyridine of the formula:

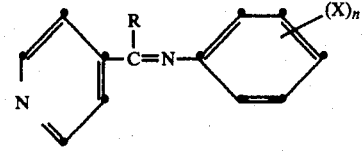

wherein
(1) R is isopropoxy and (X)$_n$ is
   (i) 4-chloro;
   (ii) 2,4-dichloro;
   (iii) 3,4-dichloro;
   (iv) 2,3-dichloro;
   (v) 3,5-chloro;
(2) R is cyano and (X)$_n$ is 4-chloro.

3. A phenyliminomethylpyridine according to claim 1 wherein m is zero, R is octyloxy and (X)$_n$ is 4-chloro.

* * * * *